United States Patent
Zettler et al.

(10) Patent No.: US 8,233,158 B2
(45) Date of Patent: Jul. 31, 2012

(54) METHOD AND APPARATUS FOR DETERMINING THE LAYER THICKNESS AND THE REFRACTIVE INDEX OF A SAMPLE

(75) Inventors: Joerg-Thomas Zettler, Berlin (DE); Johannes K. Zettler, Berlin (DE)

(73) Assignee: Laytec Aktiengesellschaft, Berlin (DE)

( * ) Notice: Subject to any disclaimer, the term of this patent is extended or adjusted under 35 U.S.C. 154(b) by 267 days.

(21) Appl. No.: 12/777,712

(22) Filed: May 11, 2010

(65) Prior Publication Data

US 2010/0290046 A1   Nov. 18, 2010

(30) Foreign Application Priority Data

May 12, 2009 (DE) .......................... 10 2009 021 751
Jun. 25, 2009 (EP) ..................................... 09163819

(51) Int. Cl.
  *G01B 11/28*   (2006.01)
(52) U.S. Cl. ...................................................... 356/630
(58) Field of Classification Search .................... 356/630
  See application file for complete search history.

(56) References Cited

U.S. PATENT DOCUMENTS 5,999,267 A * 12/1999 Zawaideh ...................... 356/630
2009/0190141 A1 * 7/2009 Bareket et al. ................ 356/630

OTHER PUBLICATIONS

Harrick, Determination of Refractive Index and Film Thickness from Interference Fringes, Oct. 1971, vol. 10, No. 10, Applied Optics.
Zhou, et al., Optical Characterization of β-FeSi2 Thin Films Prepared on Fused Quartz by Femtosecond Laser Ablation, May 2007, pp. 33-37, Elsevier B.V.
Esteban, et al., Optical Constants of a Sodium Alginate Polymer in the UV-vis range, Aug. 2008, pp. 696-699, Elsevier B.V.

* cited by examiner

*Primary Examiner* — Michael P Stafira
(74) *Attorney, Agent, or Firm* — Novak Druce + Quigg LLP

(57) ABSTRACT

The present invention relates to a method and an apparatus for determining the layer thickness and the refractive index of a sample.
It is an object of the present invention to provide a method for determining the layer thickness of a sample (layer) having high light scattering characteristics that allows a fast (real-time process) and cost-effective measurement having a high accuracy.
The method according to the present invention comprises: irradiating a first optical radiation onto the sample (4), wherein the first radiation is substantially perpendicularly irradiated onto the surface of the sample (4), and determining a first reflection spectrum (10) resulting from reflection of the first radiation on the sample (4); irradiating a second optical radiation onto the sample (4), wherein the second radiation is irradiated onto the surface of the sample (4) under an oblique angle, and determining a second reflection spectrum (12) resulting from reflection of the second radiation on the sample (4); determining a minimum of the first reflection spectrum (10), determining a minimum of the second reflection spectrum (12), and determining the layer thickness and the refractive index of the sample (4) using the minimum of the first reflection spectrum (10) and the minimum of the second reflection spectrum (12).

15 Claims, 2 Drawing Sheets

METHOD AND APPARATUS FOR DETERMINING THE LAYER THICKNESS AND THE REFRACTIVE INDEX OF A SAMPLE

CROSS-REFERENCE TO RELATED APPLICATIONS

This application claims priority to German Patent Application 102009021751.7, filed May 12, 2009, and European Patent Application 09163819.7, filed Jun. 25, 2009, the entire contents of each are incorporated herein by reference.

BACKGROUND OF THE INVENTION

1. Field of the Invention

The present invention relates to a method and an apparatus for determining the layer thickness and the refractive index of a sample.

2. Description of Related Art

Measurements of layer thickness and refractive index belong to the most important tools during quality control in the semiconductor production. In these days, such measurements are not only carried out for quality assurance after the manufacturing process steps, but also through real-time measurements during coating processes.

In this respect, different spectroscopic-optical real-time methods are known in the prior art. Light is suitably irradiated onto the sample (consisting of a thin layer on a substrate) to be investigated and then measured either in reflection or in transmission in order to achieve a contactless determination of the layer thickness. Typical measurement methods using perpendicular incidence of light are transmission-spectroscopy and reflectance-spectroscopy. Furthermore, U.S. Pat. No. 5,999,267 discloses an apparatus comprising two light sources for irradiating a film at a normal angle and at an oblique angle of incidence, respectively, wherein the calculation of the optical constants and thickness of the film is based on the power spectral density spectra of the two reflection spectra. Typical measurement methods using oblique incidence of light are ellipsometry and polarisation dependent photometry. Examples of methods using two light sources irradiating at different oblique incidence angles are discussed in "Optical constants of a sodium alginate polymer in the UV-vis range" by Ó. Esteban et al., Optical Materials 31 (2009), 696-699, and in "Optical characterization of β-FeSi$_2$ thin films prepared on fused quartz by femto second laser ablation" by Youhua Zhou et al., Physica B 399 (2007) 33-37.

The change of the light intensity or the shift of the light phase caused by the layer structure is then measured. These changes can be described by physical laws so that the change of the light intensity/the shift of the light phase are a function of the layer parameters, i.e. a function of the layer thickness and the optical material properties of the sample. Thus, the layer parameters may be determined using said functional dependence. Due to the fact that there is a strongly non-linear dependence between the change of the light intensity/shift of the light phase and the layer parameters, the mathematical determination is not performed by analytical calculations but by numerical fitting algorithms as for example Marquardt-Levenberg and Simplex of Nelder & Meat.

However, the methods disclosed in the prior art can only be reasonably used for samples that comprise a relatively low surface and interface scattering. Due to the fact that in solar cell applications (using wet chemical etching) silicon wafers are intentionally manufactured having a textured surface (on which a thin transparent film is applied) with relatively high scattering characteristics in order to increase the solar cell efficiency, the methods disclosed in the prior art cannot be appropriately used for an fast and exact determination of the layer thickness and the refractive index of such highly scattering samples which are e.g. shown in FIG. 1.

In particular, it is disadvantageous in the prior art that known methods such as ellipsometry come along with high adjustment requirements or result in a low measurement accuracy such as the camera based reflection colour recognition. Moreover, the reflection colour recognition only provides the product of layer thickness d and refractive index n but not the required single values.

It is therefore an object of the present invention to provide a method for determining the layer thickness of a sample (substrate having a thin layer thereon, wherein the thickness of the thin layer is to be determined) having high light scattering characteristics that allow a fast (real-time process) and cost-effective measurement having a high accuracy. In particular, the method and the apparatus of the present invention shall be applicable in manufacturing processes for wafer based solar cells in which the solar cell structures (samples) can be investigated for no more than a few tens of a milliseconds during process control.

SUMMARY OF THE INVENTION

Aspects of exemplary embodiments of the present invention are directed to a method for determining the layer thickness d between 30 nm and 150 nm and the refractive index n of a single layer on top of a highly rough and textured substrate (both together are understood as the sample), the method comprising: irradiating a first optical radiation onto the sample, wherein the first radiation is substantially perpendicularly irradiated onto the surface of the sample, and measuring a first reflection spectrum resulting from reflection of the first radiation on the sample; irradiating a second optical radiation onto the sample, wherein the second radiation is irradiated onto the surface of the sample under an oblique angle, and measuring a second reflection spectrum resulting from reflection of the second radiation on the sample; determining a minimum of the first reflection spectrum; determining a minimum of the second reflection spectrum; and determining the layer thickness and the refractive index of the sample using the minimum of the first reflection spectrum and the minimum of the second reflection spectrum.

In the sense of the present invention, the expression "substantially perpendicularly" is understood in that light is preferably perpendicularly irradiated, however, it may also be possible that light is irradiated onto the surface of the sample under an angle between 0-5° with respect to normal incidence.

In the sense of the present invention, the layer thickness is understood as the average layer thickness at the measuring spot(s), i.e. at the spot(s) where the first optical radiation and the second optical radiation are irradiated onto the sample. Preferably the first optical radiation and the second optical radiation are irradiated onto the same spot of the sample, however at least the spot of the first optical radiation and the spot of the second optical radiation overlap each other. Preferably the overlapping spot of first/second optical radiation has a size between 0.2 mm$^2$ and 30 mm$^2$, more preferably between 1 and 8 mm$^2$.

In the sense of the present invention, the step of determining a minimum of the first reflection spectrum is understood as determining the wavelength of the first optical radiation for which the reflection intensity is minimal and the step of determining a minimum of the second reflection spectrum is understood as determining the wavelength of the second optical radiation for which the reflection intensity is minimal.

In the sense of the present invention, the layer of a "transparent" material (which is located on the scattering substrate) means that the layer is transparent for visible light such that the absorption of visible light passing through the layer (and back) is less than 90%, preferably less than 50%, and more preferably less than 20%. Preferred materials of the layer of a transparent material are a $Si_3N_4$ or $SiN_x$ film with a thickness between 30 nm and 150 nm.

Preferably the optical material properties of the sample (refractive index n,k of the substrate for all wavelength of interest, dispersion of the refractive index of the layer, i.e., the related change of this refractive index with respect to its value at a reference wavelength) are known or are predetermined on smooth reference samples by using well known standard techniques for the determining the layer thickness and the refractive index of the sample from the minimum of the first reflection spectrum and the minimum of the second reflection spectrum.

Preferably the first optical radiation and the second optical radiation are simultaneously irradiated onto the sample.

Preferably the first optical radiation and the second optical radiation are irradiated onto the same point of incidence of the sample.

Preferably the second optical radiation is irradiated onto the sample having an angle greater than 0° and less than 90° with respect to the surface normal of the sample.

More preferably, the second optical radiation is irradiated onto the sample having an angle between 20° and 88°, still more preferably between 50° and 84° and still more preferably between 65° and 80° with respect to the surface normal of the sample.

Preferably the absolute minimum of the first reflection spectrum is used as the minimum of the first reflection spectrum. Preferably the absolute minimum of the second reflection spectrum is used as the minimum of the second reflection spectrum.

Preferably the first reflection spectrum of the sample is determined for a predetermined wavelength interval of the first radiation. Preferably the second reflection spectrum of the sample is determined for a predetermined wavelength interval of the second radiation. Preferably the wavelength interval of the first radiation and/or for the second radiation is selected to be 300 nm to 1000 nm, preferably 400 nm to 900 nm and still more preferably 500 nm to 800 nm.

Preferably crystalline or multi-crystalline silicon is used as the substrate of the sample. Preferably, the layer on the substrate of the sample (where the layer's thickness and refractive index are to be determined) is transparent, more preferably the layer is a $Si_3N_4$ or $SiN_x$ film. More preferably, the layer thickness ranges between 60 nm and 90 nm, and more preferably between 75 nm and 85 nm.

In particular, according to the present invention, a sample is preferably understood as a thin-film structure comprising a substrate and at least one but preferably a single layer, wherein the thickness and the refractive index of the (single) (top) layer are to be determined. More preferably, the sample used in the present invention comprises a substrate with a certain degree of roughness/texture thereon having a single transparent layer on top, wherein the thickness and the refractive index of the single layer are to be determined. As the refractive index of the layers changes with wavelength (optical dispersion), the refractive index is to be determined at a characteristic reference wavelength which is preferably selected from the range 300 nm-1000 nm, more preferably the characteristic reference wavelength is set to be 625 nm. Furthermore the optical dispersion of the used materials is taken into account when comparing the measured minimum positions of the first and second reflection spectrum to the minimum positions of the respective calculated spectra.

Preferably the surface of the sample comprises a roughness/texture between 0 nm and $10^5$ nm, more preferably the surface of the sample comprises a texture between $10^3$ nm and $10^4$ nm (which extends in vertically and/or laterally) wherein the surface of the sample comprises a scattering for light in the 300 nm to 1000 nm wavelength range.

Preferably the sample comprises a macroscopically planar surface. Preferably the sample comprises a layer thickness between 30 nm and 150 nm. Preferably the layer on top of the rough/textured substrate comprises a refractive index between 1.5 and 2.5.

Preferably the product n*d of layer thickness d and layer refractive index n of the sample is determined using the minimum of the first reflection spectrum. Preferably a plurality of pairs of values of layer thickness and refractive index of the sample complying with the previously determined product of layer thickness and refractive index are generated. For each of these pair of n,d-values the expected second reflection minimum is also calculated taking into account the known (small) optical dispersions of all materials. Finally, the specific pair of values having the same calculated reflection minimum as the measured minimum of the second reflection spectrum is judged to be the pair of value representing the layer thickness and refractive index of the sample.

Further aspects of exemplary embodiments of the present invention are directed to an apparatus adapted for determining the layer thickness between 30 nm and 150 nm and the refractive index of a sample, comprising: a first optical light source and a first optical detector, the first optical light source and the first optical detector being adapted to perpendicularly irradiate a first optical radiation onto the sample and adapted to determine a first reflection spectrum resulting from reflection of the first radiation on the sample; a second optical light source and a second optical detector, the second optical light source and the second optical detector being adapted to irradiate a second optical radiation onto the sample under an oblique angle and adapted to determine a second reflection spectrum resulting from reflection of the second radiation on the sample; wherein the apparatus further comprises a data processing unit adapted to determine a minimum of the first reflection spectrum and a minimum of the second reflection spectrum, and wherein the data processing unit is furthermore adapted to determine the layer thickness and the refractive index of the sample from the determined minimum of the first reflection spectrum and the determined minimum of the second reflection spectrum. Preferably the first optical light source and/or the second optical light source is a halogen lamp which is preferably (at least) irradiating between 300-3000 nm. Preferably the first optical detector and/or the second optical detector is a Si-CCD-detector which preferably (at least) detects in a range between 350-1050 nm.

Preferably, the sample can be tilted (rotated) by 0-60° with respect to the first and second optical light source, wherein the axis of rotation is defined by the intersecting line between the plane of the sample surface and the plane defined by incident and specularly reflected second optical radiation. Preferably the angle of rotation is selected to be equal or substantially equal to the angle of the facets of the textured surface of the sample. In this case it is assumed that the sample comprises a textured surface having a plurality of pyramid-like shaped facets with a predetermined angle. Alternatively, in applications where the sample orientation cannot be changed, the orientation of the apparatus can be tilted with respect to the said intersection line for establishing the same relative geometry between sample and apparatus as described before for a tilted sample.

BRIEF DESCRIPTION OF THE DRAWINGS

The accompanying drawings, together with the specification, illustrate exemplary embodiments of the present invention, and, together with the description, serve to explain the principles of the present invention.

DETAILED DESCRIPTION

In the following detailed description, only certain exemplary embodiments of the present invention are shown and described, by way of illustration. As those skilled in the art would recognize, the invention may be embodied in many different forms and should not be construed as being limited to the embodiments set forth herein.

Figure 1:
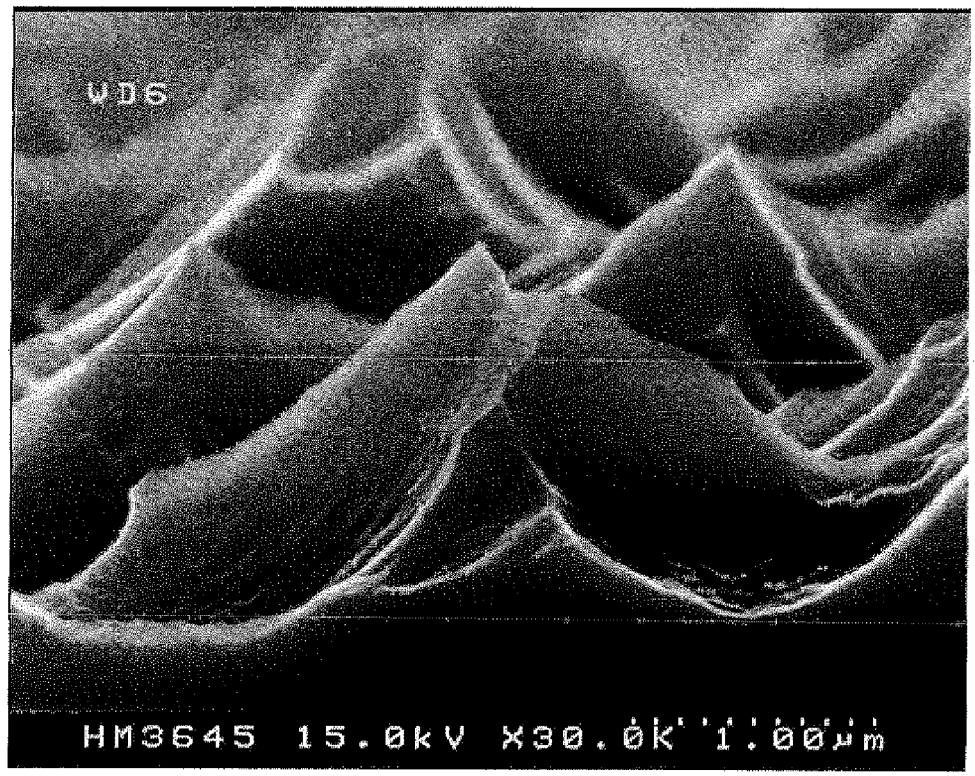
FIG. 1 is a microscopic photograph of a textured surface of crystalline silicon having relatively high scattering characteristics.

FIG. 1 shows a textured solar cell substrate (designated with reference number 4 in FIG. 2) where typically a transparent film ($SiN_x$, $SiO_x$, $SiO_xN_y$ and others) is grown on top as an anti-reflecting coating. The thickness and the refractive index of the silicon layer are to be determined. As can be seen from the TEM photograph of FIG. 1, the textured surface of crystalline silicon comprises a non regular (and/or non uniform) protrusion pattern resulting in relatively high scattering characteristics. However, prior art methods such as ellipsometry result in very high adjustment requirements in case of such highly scattering surfaces. Other known methods such as camera based reflection colour recognition result in a very low measurement accuracy and cannot separate effects of film thickness and film refractive index. Therefore there is a need for a simple and fast but also reliable method for determining the layer thickness and the layer refractive index of highly rough/textured samples with a sufficiently high accuracy.

Figure 2:
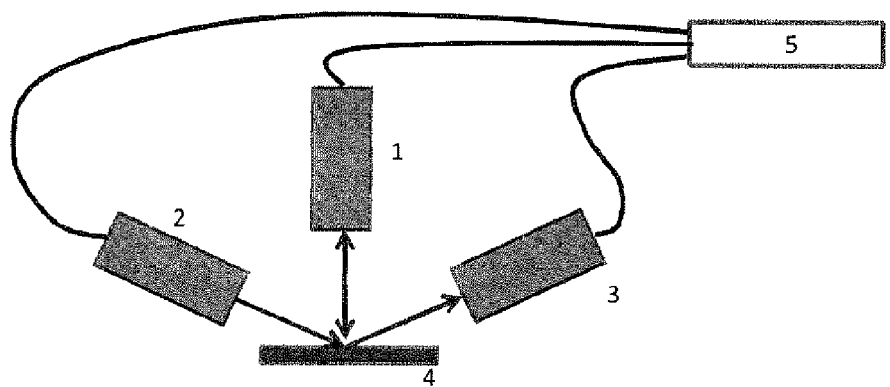
FIG. 2 is a schematic view of an apparatus adapted for determining the layer thickness and the refractive index of a sample according to an exemplary embodiment of the present invention.

FIG. 2 shows an apparatus adapted for determining the layer thickness and the refractive index of the sample 4 according to an exemplary embodiment of the present invention. In particular, the apparatus comprises a light irradiating and reflection sensing unit 1 adapted for vertical incidence, a light irradiating unit 2 for oblique incidence, a light detection unit 3 for oblique incidence and a data processing unit 5, wherein the units 1, 2 and 3 are optimized for scattering light. The units 1, 2 and 3 are all connected to and controlled by the data processing unit 5.

Figure 3:
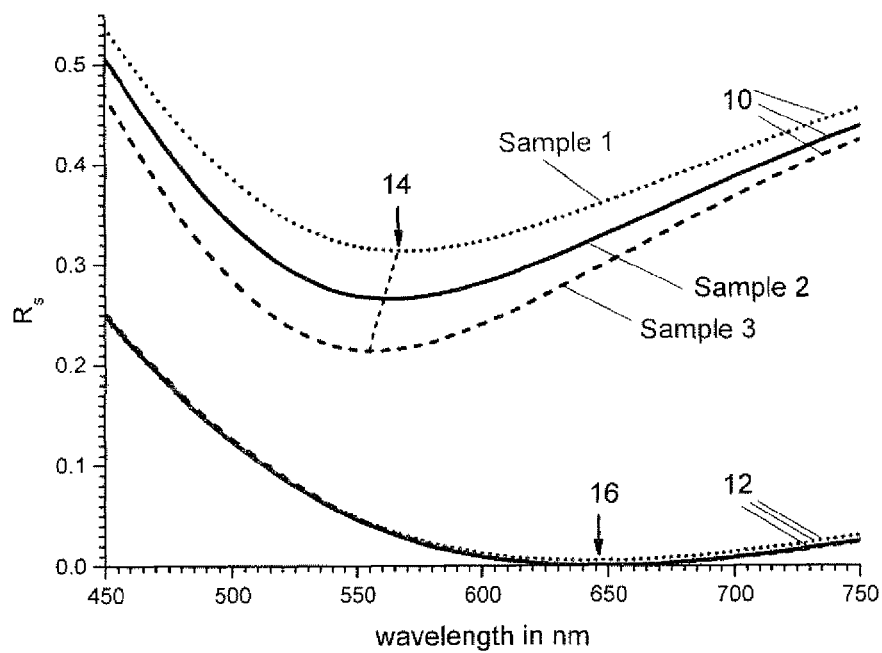
FIG. 3 shows the reflection spectrum of a first sample, a second sample and a third sample for perpendicular incidence and oblique incidence.

FIG. 3 shows the calculated reflection spectra (using state-of-the-art thin-film software algorithms) of different smooth (non-textured) samples 1-3 for perpendicular and oblique incidence, in particular sample 1 has a refractive index of 2.12 and a thickness of 76.2 nm, sample 2 has a refractive index of 2.02 and a thickness of 80.0 nm, and sample 3 has a refractive index of 1.92 and a thickness of 84.2 nm, wherein each of sample 1 to sample 3 has the same product of layer thickness and refractive index. All refractive indices refer to a wavelength of 625 nm and the typical dispersion of $Si_3N_4$ films is assumed. It can be seen in FIG. 3 that all three samples 1-3 have substantially the same reflection minimum at perpendicular incidence at about 650 nm, however the three samples each have a significantly different reflection minimum under oblique irradiation between 550 nm (sample 3) and 575 nm (sample 1).

The main idea of the invention is to provide a solution which determines the layer thickness and the refractive index of the sample 4 by only using (measuring) the spectral position of characteristic points (=minimum) in the reflection spectrum under perpendicular and under oblique incidence, which are surprisingly found to be much less changed by texture effects than the usually measured reflection intensity. In contrast to this, ellipsometry uses phase differences and intensity relations under oblique incidence and photometric measurements use the dependence between the reflection intensity and the wavelength at perpendicular incidence, all significantly modified by texture and roughness. Advantageously, the method according to the present invention is less sensitive to surface texture effects and therefore the determination accuracy (for the layer thickness and the refractive index) are significantly higher and the adjustment requirements are relatively lower compared to the methods of the prior art.

Another distinct advantage is that it is not necessary to determine the exact reflection amplitudes which may vary due to scattering. It is only necessary to determine (measure) the minimum position which is less sensitive to scattering and can be performed very fast.

Figure 4:
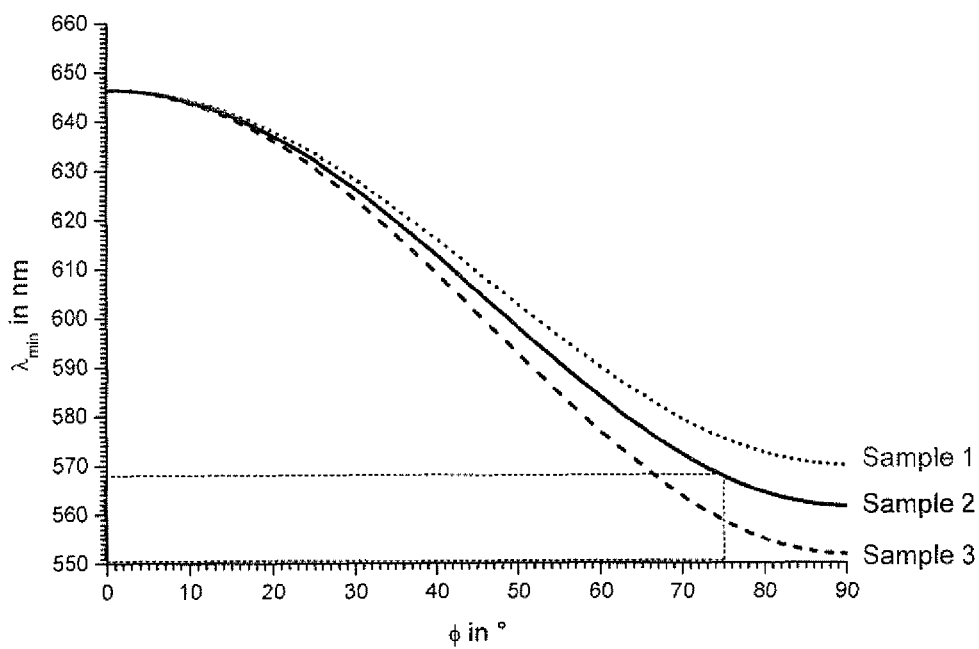
FIG. 4 is a diagram showing the dependence between the wavelength of the reflection minimum and the angle of incidence for the first, the second and the third sample.

FIG. 4 is showing the dependence between the wavelength ($\lambda_{min}$) of the reflection minimum and the angle of incidence ($\phi$) for the first, the second and the third sample.

The calibration curves in FIG. 4 have been calculated using the $\lambda/2$ phase shift criterium between the partial waves reflected from the ambient/layer and the layer/substrate interface of the sample:

$$\lambda_{min} = 4n \ast \mathrm{SQRT}[x^2/4 + d^2] - 2x \ast \sin \phi \quad (1)$$

with $x = 2d \tan[a \sin(\sin \phi/n)]$ $\phi$ is the angle of incidence. With $\phi \to 0$ the well known anti-reflex condition $\lambda_{min}^{\phi=0} = 4nd$ results. FIG. 4 has been calculated according to equ. (1) and therefore is based on the simplifying assumption that n is constant for all $\lambda$, ignoring the typically small (~2%) dispersion of transparent films in this spectral range. In addition, the very small shift in normal incidence reflectance minimum with the refractive index of the layer due to phase-shifting effects of the layer-substrate interface is also ignored. However, both these effects are very small and an accurate calibration curve very similar to FIG. 4 can be calculated with appropriate thin-film software using the exact multi-layer algorithms.

Hence, for thin transparent films on high-refractive substrates (e.g., $SiN_x$ on silicon) the product of layer thickness and refractive index $(n \ast d) = \lambda_{min}^{\phi=0}/4$ can be directly calculated from the minimum position of the first reflectance spectrum taken at perpendicular incidence.

The shifting of the reflection minimum $\lambda_{min}$ with the angle of incidence significantly depends on the refractive index of the samples. This dependence can by exactly calculated for a plurality of materials and layer thicknesses and these results can be pre-stored in a table for a plurality of $(n,d)$-$(\lambda_{min}^1, \lambda_{min}^2)$ pairs. Therefore, by comparison of the measured pair of reflection minima (taken at normal incidence and at given oblique incidence) to this table the accurate refractive index n and thickness d of the layer can be determined.

That is, the layer thickness and the refractive index can be exactly determined by a simple numerical procedure from the wavelength of the reflection minimum of perpendicular incidence and the wavelength of the reflection minimum of oblique incidence. In order to achieve a high accuracy, the oblique angle differs from the perpendicular incidence by at least 50°, more preferably by at least 70°.

The data processing unit 5 conducts a pre-calculation of theoretical minimum wavelengths for a predetermined range of film refractive indices and a (predetermined) film thickness interval (of interest) of the sample (4), taking into account also the optical dispersion properties of the film and substrate materials. Furthermore, the data processing unit 5 determines the minimum wavelengths at perpendicular and oblique incidence from the measured reflection intensities of the units 1 and 3 for the sample 4 and finally the data processing unit 5 determines the refractive index and the thicknesses of the sample 4 from a comparison with the pre-calculated theoretical minimum wavelengths for the said pairs of refractive indices and thicknesses by comparing which pair has the same theoretically calculated minimum wavelengths (at perpendicular and oblique incidence) as the minimum wavelengths determined from the measured reflection intensity of the units 1 and 3.

List of Reference Signs 1 light irradiating and reflection sensing unit for vertical incidence, optimised for scattering light 2 (reflection) light irradiating unit for oblique incidence (here: 75°), optimised for scattering light 3 (reflection) light detection unit for oblique incidence (here: 75°), optimised for scattering light 4 (single) layer being disposed on a textured substrate (the thickness and the refractive index of the layer are to be determined)/sample comprising said layer and said substrate 5 data processing unit/analysing computer 10 reflection spectrum resulting from reflection of the second radiation on the sample 12 reflection spectrum resulting from reflection of the first radiation on the sample 14 minimum of the reflection spectrum resulting from reflection of the second radiation on the sample 16 minimum of the reflection spectrum resulting from reflection of the first radiation on the sample

What is claimed is:

1. Method for determining the thickness and the refractive index of a layer (4) of a transparent material having a layer thickness between 30 nm and 150 nm which is disposed on a scattering substrate, the method comprising:
    irradiating a first optical radiation onto the sample (4) which comprises said scattering substrate and said layer of a transparent material thereon, wherein the first radiation is irradiated onto the surface of the sample (4) under an angle between 0-5° with respect to normal incidence, and determining a first reflection spectrum (10) resulting from reflection of the first radiation on the sample (4),
    irradiating a second optical radiation onto the sample (4), wherein the second radiation is irradiated onto the surface of the sample (4) under an oblique angle, and determining a second reflection spectrum (12) resulting from reflection of the second radiation on the sample (4),
    determining a minimum of the first reflection spectrum (10),
    determining a minimum of the second reflection spectrum (12), and
    determining the thickness and the refractive index of the layer of a transparent material using the minimum of the first reflection spectrum (10) and the minimum of the second reflection spectrum (12).

2. The method of claim 1, wherein the material of the layer is taken into account for determining the thickness and the refractive index of the layer of a transparent material from the minimum of the first reflection spectrum (10) and the minimum of the second reflection spectrum (12).

3. The method of claim 1, wherein the first optical radiation and the second optical radiation are simultaneously irradiated onto the sample (4).

4. The method of claim 3, wherein the first optical radiation and the second optical radiation are irradiated onto the same point of incidence of the sample (4) and/or wherein the sample or the apparatus is rotated with respect to the plane defined by incident and specularly reflected second optical radiation, wherein the axis of rotation is defined by the intersecting line between the plane of the sample surface and the plane defined by incident and reflected second optical radiation.

5. The method of claim 4, wherein the second optical radiation is irradiated onto the sample (4) having an angle greater than 0° and less than 90° with respect to a direction normal to the sample (4).

6. The method of claim 5, wherein the second optical radiation is irradiated onto the sample (4) having an angle between 20° and 88°, preferably between 50° and 84° and more preferably between 65° and 80° with respect to a direction normal to the sample (4).

7. The method of claim 6, wherein the absolute minimum of the first reflection spectrum (10) is used as the minimum of the first reflection spectrum (10) and/or wherein the absolute minimum of the second reflection spectrum (10) is used as the minimum of the second reflection spectrum (10).

8. The method of claim 1, wherein the first reflection spectrum (10) of the sample (4) is measured for a predetermined wavelength interval of the first irradiation and/or wherein the second reflection spectrum (12) of the sample (4) is measured for a predetermined wavelength interval of the second irradiation.

9. The method of claim 8, wherein the wavelength interval is selected to be 300 nm to 1000 nm, preferably 400 nm to 900 nm and still more preferably 500 nm to 800 nm.

10. The method of claim 9, wherein crystalline or multicrystalline silicon is used as the substrate of the sample (4).

11. The method of claim 9, wherein the surface of the sample (4) comprises a vertical and/or lateral texture between 0 nm and $10^5$ nm, and/or wherein the surface of the sample (4) comprises a scattering or similar partial deflection for light in the 300 nm to 1000 nm wavelength range.

12. The method of claim 9, wherein the sample (4) comprises a macroscopically planar surface and/or wherein the layer of a transparent material comprises a refractive index between 1.5 and 2.5 in the wavelength range between 300 nm and 1000 nm.

13. The method of claim 9, wherein the product of layer thickness and refractive index of the layer of a transparent material is determined using the minimum of the first reflection spectrum (10).

14. The method of claim 13, wherein a plurality of pairs of values of thickness and refractive index of the layer of a transparent material complying with the previously determined product of layer thickness and refractive index are generated, and the pair of value of which the two calculated reflection minima are equal to the measured two reflection minima is judged to be the pair of value representing the thickness and refractive index of the layer of a transparent material.

15. An apparatus adapted for determining the thickness and the refractive index of a layer (4) of a transparent material having a layer thickness between 30 nm and 150 nm which is disposed on a scattering substrate, the apparatus comprising:

a first optical light source (1) and a first optical detector (1), the first optical light source (1) and the first optical detector (1) being adapted to irradiate a first optical radiation onto a sample (4) under an angle between 0-5° with respect to normal incidence which comprises said scattering substrate and said layer of a transparent material thereon and adapted to determine a first reflection spectrum (10) resulting from reflection of the first radiation on the sample (4);

a second optical light source (2) and a second optical detector (3), the second optical light source (2) and the second optical detector (3) being adapted to irradiate a second optical radiation onto the sample (4) under an oblique angle and adapted to determine a second reflection spectrum (12) resulting from reflection of the second radiation on the sample (4);

characterized in that the apparatus further comprises a data processing unit (5) adapted to determine a minimum of the first reflection spectrum (10) and a minimum of the second reflection spectrum (12), and wherein the data processing unit (5) is furthermore adapted to determine the thickness and the refractive index of the layer of a transparent material from the determined minimum of the first reflection spectrum (10) and the determined minimum of the second reflection spectrum (12).

* * * * *